United States Patent [19]

Pippert

[11] Patent Number: 5,272,917

[45] Date of Patent: Dec. 28, 1993

[54] CHECKING APPARATUS FOR INJECTION OR INFUSION-TYPE PUMPS

[75] Inventor: Manfred Pippert, Glashütten, Fed. Rep. of Germany

[73] Assignee: Medical Support GmbH, Rodgau, Fed. Rep. of Germany

[21] Appl. No.: 814,756

[22] Filed: Dec. 30, 1991

[30] Foreign Application Priority Data

Dec. 28, 1990 [DE] Fed. Rep. of Germany ....... 4042101

[51] Int. Cl.⁵ .......................................... G01M 19/00
[52] U.S. Cl. ...................................................... 73/168
[58] Field of Search ................ 73/3, 4 R, 168, 865.9, 73/232, 239, 252, 168; 417/63

[56] References Cited

U.S. PATENT DOCUMENTS

| | | | |
|---|---|---|---|
| 3,817,097 | 6/1974 | Heroux | 73/49.7 |
| 4,051,712 | 10/1977 | Zias et al. | 73/4 R |
| 4,073,304 | 2/1978 | Lerner et al. | 73/3 |
| 4,253,156 | 2/1981 | Lisle et al. | 73/3 |
| 4,269,058 | 5/1981 | Richman | 73/4 R |
| 4,307,601 | 12/1981 | Jackson | 73/3 |
| 4,324,127 | 4/1982 | Gazzara et al. | 73/3 |
| 4,453,403 | 6/1984 | Bussey et al. | 73/119 A |
| 4,829,808 | 5/1989 | West | 73/3 |
| 4,865,581 | 9/1989 | Lundquist et al. | 604/67 |
| 4,890,984 | 1/1990 | Alderson et al. | 417/63 |
| 4,903,529 | 2/1990 | Hodge | 73/37 |
| 5,139,484 | 8/1992 | Hazon et al. | 604/65 |

FOREIGN PATENT DOCUMENTS 556195  9/1943  United Kingdom ................ 73/4 R

Primary Examiner—Robert Raevis
Attorney, Agent, or Firm—Juettner, Pyle & Lloyd

[57] ABSTRACT

The checking apparatus for injection- or infusion-type pumps comprises a glass piston syringe, a linear potentiometer whose spindle is rigidly connected to the piston of the glass piston syringe, a pressure transducer in communication with the syringe inlet, and an electronic computing and evaluating means connected through a water-filled tube to the glass piston syringe and presses water into the glass piston syringe at a predetermined delivery rate. The apparatus displays on three display panels. These important parameters can be measured quickly and precisely with the aid of said apparatus.

13 Claims, 1 Drawing Sheet

CHECKING APPARATUS FOR INJECTION OR INFUSION-TYPE PUMPS

BACKGROUND OF THE INVENTION

This invention relates to an apparatus for checking and measuring the parameters of injection- or infusion-type pumps, in particular, for measuring delivery rate, delivery pressure, delivery amount and shut-off pressure. These parameters must be checked in all injection- and infusion-type pumps at regular intervals because health and life of a patient might depend on the correct value of these parameters.

So far, the delivery rate of an injection-type pump has been determined indirectly through a displacement measurement of the advancing syringe-type piston. It is known that to this end a mechanical dial gauge is clamped within the syringe receiving cavity of the injection-type pump and that the injection-type pump is operated by means of a timer for a specific period of time. After the end of this period the distance covered by the syringe-type piston, which has been advanced by a threaded spindle of the injection-type pump, is read on the dial gauge. This displacement measurement has the disadvantage that a precise reading of the measured values and strict observance of the selected time interval are difficult to carry out. As a result, the delivery rate of the injection-type pump cannot be determined in a reliable way and with the necessary preciseness. Moreover, this indirect measurement of the delivery rate is very troublesome and time-consuming.

SUMMARY OF THE INVENTION

It is the object of the present invention to provide a checking apparatus with the aid of which the relevant parameters of all common types of injection or infusion pumps can be measured precisely and easily, i.e. especially delivery rate, delivery pressure, delivery amount and shut-off pressure of such pumps.

The checking apparatus of the invention comprises a syringe, preferably a glass piston syringe, the capacity of which is expediently 50 ml., a connection coupled to the syringe casing for supplying liquid from the pump to be checked into the interior of the syringe casing, whereby the syringe piston is pushed back accordingly into the syringe casing, a displacement measuring device rigidly connected to the syringe piston in a mechanical way, so that the movement of the piston is transmitted to the displacement measuring device, a computing and evaluating means connected to the displacement measuring device and display means coupled to the latter for displaying the delivery rate and/or delivery amount of the liquid fed into the syringe casing. These members are expediently arranged within a casing that should be equipped with a Luer-Lock tube connection for coupling the pump to be checked. The pump to be checked is connected by means of a water-filled tube to said Luer-Lock connection whereupon the desired delivery rate is set in the pump, so that the latter feeds liquid into the syringe means of the checking apparatus after the checking apparatus has been switched on. Since the piston of the syringe means is rigidly connected to the displacement measuring device in a mechanical way, the displacement measuring device is actuated accordingly by the movement of the syringe piston and supplies associated electrical signals to the electronic computing and evaluating means.

Since the inner diameter of the syringe is known and the distance covered by the piston of the syringe is determined by means of the displacement measuring device, the computing and evaluating means calculates the delivery quantity of the liquid on the basis of these values. The delivery rate is a time function of this delivery rate and the delivery quantity of the liquid can be displayed by the display device on corresponding display panels.

These values are quickly determined in a very precise way. The respective test specimen need only be connected through a water-filled tube to the checking apparatus. The checking operation can thus be carried out by laymen as well.

In an advantageous development of the invention, a spring means counteracts the advance of the syringe piston when liquid is supplied into the syringe casing, with the spring always acting on the piston to urge the latter into its initial position. The delivery pressure is adjusted through the spring means.

In an expedient embodiment of the invention the spring means is a pressure spring which may be arranged between the rear end of the piston, or a piston rod connected to the piston and a stop fixedly mounted on the casing, e.g. a housing wall of the checking apparatus.

Furthermore, a great advantage is here that the checking apparatus additionally comprises a pressure measuring device for measuring the liquid supplied to the syringe casing. This pressure measuring device should be a pressure transducer the measuring data of which are displayed by an associated delivery-pressure display device of the apparatus. The assembly may here be implemented such that the pressure transducer is connected through a T-shaped line member to the syringe inlet.

The displacement measuring device is expediently a linear potentiometer to the spindle of which the syringe position should be rigidly connected. The assembly is expediently implemented within the apparatus casing in such a way that the linear potentiometer is arranged next to the syringe means in spaced relationship therewith in such a way that the longitudinal axes of the two members are in parallel with each other. The syringe piston is expediently coupled through a rigid connection arm to the spindle of the potentiometer. Each movement of the syringe piston is thereby exactly transmitted to the linear potentiometer.

It is within the scope of the present invention to use other types of linear displacement measuring devices instead of a linear potentiometer.

Furthermore, a great advantage is here that the apparatus comprises a fixed stop which limits the stroke of the syringe piston. When at the end of a measuring operation the syringe piston abuts on the stop, which is fixedly mounted on the casing, the delivery pressure increases whereupon the pump to be checked switches to alarm condition. In accordance with the invention, the checking apparatus additionally includes an alarm input to which the alarm output of the pump to be checked can be connected electrically. In accordance with the invention, the alarm signal from the test specimen is thus electrically evaluated and used for electronically reading in the three displays: delivery pressure, delivery rate and delivery amount. The pump to be checked is subsequently disconnected, whereupon the pressure spring presses the syringe piston back into its initial position.

A glass piston syringe which, as already mentioned above, has a capacity of preferably 50 ml is expediently used as the syringe means. The glass piston syringe is expediently in communication with a Luer-Lock connection which has a water-filled tube coupled thereto.

An important aspect is here that not only the coupled tube, but also the subsequent syringe inlet, including the syringe piston, are filled with water without any bubbles being present, so that there is no (compressible) air in the whole conduit system. This can be accomplished in an easy way in that (in contrast to the purely diagrammatic figure) the glass piston syringe is vertically (or obliquely) arranged with the syringe inlet in the apparatus, so that the whole air escapes when the water is filled into the syringe inlet. Of course, this can also be achieved with one or several vent valves, or the like.

In injection- or infusion-type pumps the delivery rate considerably depends on the counteracting pressure. To be able to measure the delivery rate within the operating pressure range assigned to the pump, the operator who operates the checking apparatus must determine at the beginning of a checking operation by looking at the display device how great the initial delivery pressure is. This initial delivery pressure is set to the correct pressure value of the pump, if necessary, e.g. by adjusting the spring seat. This can be accomplished in a quick and easy way and ensures that the delivery rate is measured within the indicated operating pressure range of the pump.

Other features, advantages and details of the invention will become apparent from the following description of a preferred embodiment of the invention taken in conjunction with the drawing.

THE DRAWING

The sole FIGURE is a diagrammatic illustration of the apparatus of the present invention.

DESCRIPTION OF THE PREFERRED EMBODIMENT

Figure 1:
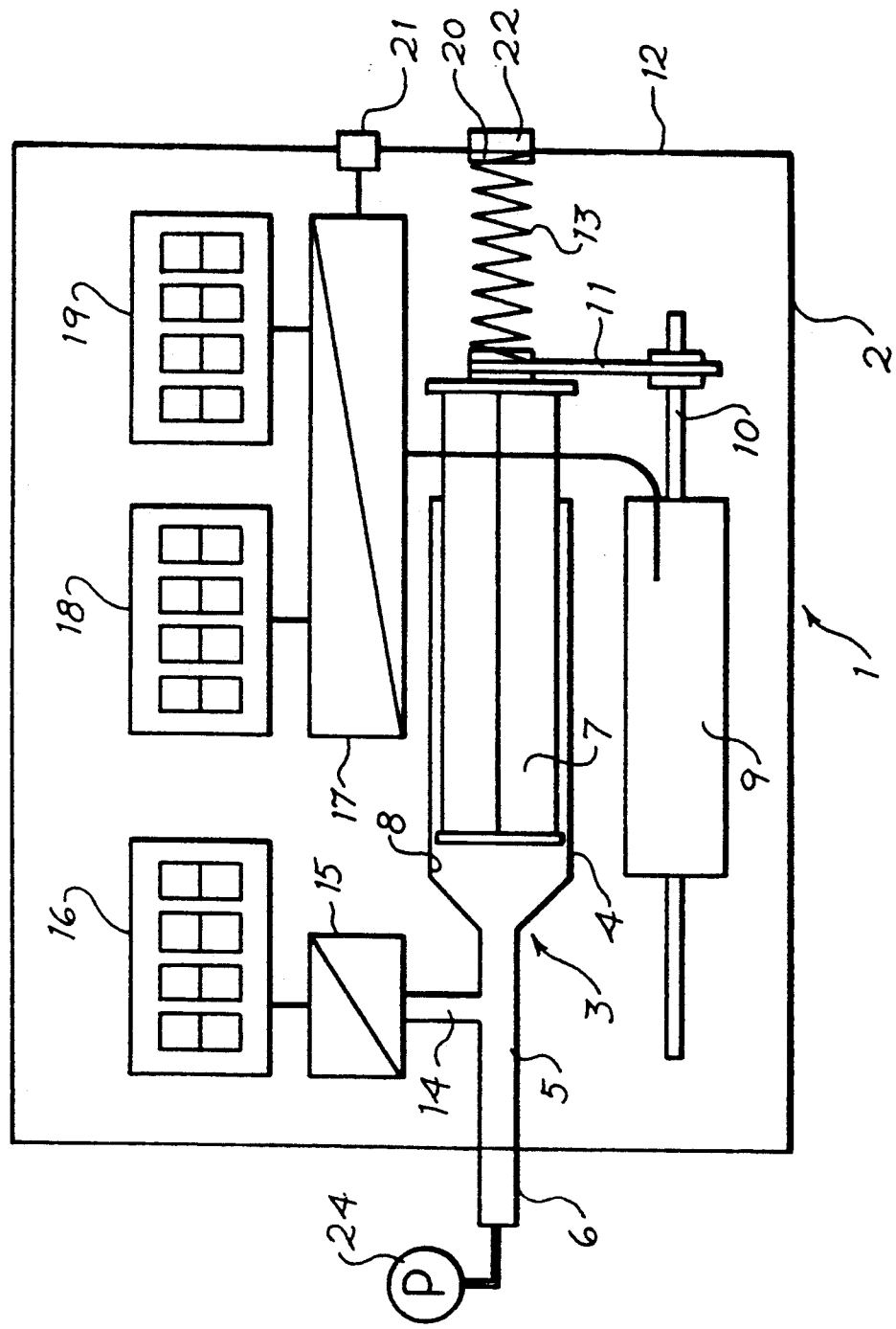

The checking apparatus or measuring device which is generally designated by 1 in the purely diagrammatic figure comprises a plastic casing 2 which contains a glass piston syringe 3 in the syringe casing of which a syringe inlet 5 terminates. This inlet is connected to a Luer-Lock connection 6, which is also illustrated in a purely diagrammatic way.

A piston 7 which defines a water receiving chamber 8 in syringe casing 4 is displacably guided in said casing 4.

A linear potentiometer 9 whose spindle 10 is rigidly connected via a connection arm 11 to the rear end of the piston 7 is arranged next to glass piston syringe 3 in parallel relationship therewith. An axial movement of piston 7 is thus converted into a parallel movement of the spindle 10 of linear potentiometer 9.

A helical pressure spring 13 is disposed between the rear end of piston 7 and the wall 12 of casing 2 and acts on piston 7 to move the latter towards its initial position shown at the left side in the figure, and counteracts a movement of piston 7 to the right. The delivery pressure of the liquid (water) supplied into inner chamber 8 is thus adjusted by means of spring 13.

A pressure transducer 15 is connected to syringe inlet 5 via T-piece 14. This pressure measuring amplifier is in communication with an associated display 16 which displays the respective delivery pressure on the upper side of casing 2 by means of a 7-segment LC display.

Linear potentiometer 9 is connected to an electronic computing and evaluating means 17 to which linear potentiometer 9 supplies the output values corresponding to the movement of piston 7. The respectively delivered amount and the respective delivery rate are displayed on the connected displays 18 and 19.

To determine or check the relevant parameters of an injection-type or infusion-type pump, the test specimen is connected by means of a water-filled tube to the Luer-Lock connection 6. After the desired delivery rate has been set on the pump, the latter presses the liquid into the interior 8 of glass piston syringe 3, whereby piston 7 is pushed to the right in the figure. The respective delivery pressure is displayed via pressure transducer 15 on display panel 16.

Since glass piston 7 of syringe 3 is rigidly connected to spindle 10 of the linear potentiometer in a mechanical way, and since the later supplies the electrical signals corresponding to the movement thereof to the electronic computing and evaluating means 17, the delivery rate and corresponding delivery amount are continuously displayed on display panels 18 and 19. Since the inner diameter of glass piston syringe 3 is known, these values can be easily calculated on the basis of the distance covered by piston 7.

At the end of the measuring operation, the rear end of piston 7 abuts, either directly or through an intermediate member, on a stop 20 which is fixedly mounted on the casing. As a result, the piston cannot be displaced any further. This has the consequence that the delivery pressure increases and the pump to be checked switches to alarm condition. The alarm output of the test specimen is electrically connected to an alarm input 21 of checking apparatus 1. The alarm signal received from the test specimen is electrically evaluated and used for electronically reading in the three displays, i.e. shut-off pressure of the pump, delivery rate and delivery amount. The checking operation is thereby concluded, with spring 13 pressing piston 7 back into its initial position after the connection tube has been uncoupled from the Luer-Lock connection 6.

The helical pressure spring 13 is adjusted such that a suitable initial pressure counteracts the advance of piston 7, with the spring pressure exponentially increasing with the advance motion of the piston.

To this end, stop 20 is designed as an adjustable spring seat which can be adjusted by means of a knurled screw 22 arranged on the outside of casing 2.

In an alternative embodiment of the invention, a mechanical friction brake may be used instead of helical pressure spring 13. This friction brake may act on spindle 10 of linear potentiometer 9 or also directly on piston 7, thereby counteracting, in contrast to helical pressure spring 13, the advance movement of the piston with a force that remains constant throughout the displacement. The frictional force of this friction brake can, e.g., be set by means of a clamping mechanism. It should here be noted that the checking apparatus is also suited for other types of pumps.

I claim:

1. A device for use in combination with a liquid pump for checking the parameters thereof, said pump having an outlet through which liquid is delivered under pressure, said device comprising a syringe comprising a casing, and inner chamber, and a piston displacably guided in said chamber; a conduit connected between the outlet of the pump and the syringe chamber, with liquid pressure from the pump serving to move the piston in a first direction; measuring means connected to said piston for measuring the volume of pumped liquid displaced by said piston to determine delivery rate of said pump; means for exerting a counteracting force on said piston in a direction opposite to said first direction; means for adjusting the degree of said counteracting force; and pressure sensing means connected to said conduit for sensing the pressure of said liquid.

2. The device of claim 1 wherein said means for exerting a counteracting force on said piston comprises a spring, a spring seat supporting one end of the spring, and the other end of said spring in engagement with said piston.

3. The device of claim 2 wherein said spring seat is adjustable toward and away from said piston.

4. The device of claim 1 wherein means are connected to the measuring means for displaying the delivery rate of said pump.

5. The device of claim 1 wherein the pressure sensing means for sensing the pressure of said liquid comprises a pressure transducer.

6. The device of claim 5 additionally comprising display means connected to said pressure transducer for displaying said liquid pressure.

7. The device of claim 1 wherein a T-shaped connection is provided in said conduit and connecting the outlet of the pump to said syringe and to the pressure sensing means.

8. The device of claim 1 wherein said measuring means comprises a linear potentiometer having a movable spindle, said syringe piston being rigidly connected to said spindle.

9. The device of claim 8 wherein said linear potentiometer is arranged in a parallel relationship with said syringe.

10. The device of claim 1 additionally comprising stop means for limiting advance of said piston in said first direction.

11. The device of claim 1 additionally comprising means for sounding an alarm when the pressure of the pump exceeds a maximum allowable pressure.

12. The device of claim 1 wherein the casing of said syringe is composed of glass.

13. The device of claim 1 wherein said pump has a shut-off pressure, and means are provided for measuring, storing and displaying said shut-off pressure.

* * * * *